(12) United States Patent
Zhang et al.

(10) Patent No.: US 6,538,128 B1
(45) Date of Patent: Mar. 25, 2003

(54) DETRITYLATION SOLVENTS FOR NUCLEIC ACID SYNTHESIS

(75) Inventors: Guangrong Zhang, Shrewsbury, MA (US); Jin-Yan Tang, Shrewsbury, MA (US)

(73) Assignee: Avecia Biotechnology, Inc., Milford, MA (US)

( * ) Notice: Subject to any disclaimer, the term of this patent is extended or adjusted under 35 U.S.C. 154(b) by 0 days.

(21) Appl. No.: 09/148,344

(22) Filed: Mar. 22, 1999

Related U.S. Application Data

(60) Provisional application No. 60/058,142, filed on Sep. 8, 1997.

(51) Int. Cl.[7] .................. C07H 21/00; C07H 21/02; C07H 21/04; C07H 19/00
(52) U.S. Cl. .................. 536/25.3; 536/25.31; 536/22.1; 536/25.33; 536/25.4; 536/26.1; 536/126.12
(58) Field of Search .............. 536/25.3, 25.31, 536/22.1, 25.33, 25.4, 26.1, 26.12

(56) References Cited

U.S. PATENT DOCUMENTS 5,149,798 A * 9/1992 Agrawal et al.

OTHER PUBLICATIONS

Reese, Tetrahedron Lett. 34:3143–3179 (1978).*
Goodchild, Tetrahedron Lett. 28:3539–3542 (1987).*
Connolly et al., Biochemistry 23:3443 (1984).*

* cited by examiner

Primary Examiner—Samuel Barts
Assistant Examiner—Michael C. Henry
(74) Attorney, Agent, or Firm—Hamilton, Brook, Smith & Reynolds, P.C.

(57) ABSTRACT

The invention provides improved processes for oligonucleotide synthesis utilizing arenes as solvents for detritylation of oligonucleotides.

11 Claims, 1 Drawing Sheet

DETRITYLATION SOLVENTS FOR NUCLEIC ACID SYNTHESIS

This application claims benefit of Provisional Application No. 60/058,142 filed Sep. 8, 1997.

BACKGROUND OF THE INVENTION

1. Field of the Invention

The invention relates to the chemical synthesis of oligonucleotides and to materials and processes that are useful in such synthesis.

2. Summary of the Related Art

Oligonucleotides have become indispensable tools in modern molecular biology, being used in a wide variety of techniques, ranging from diagnostic probing methods to PCR to antisense inhibition of gene expression. This widespread use of oligonucleotides has led to an increasing demand for rapid, inexpensive and efficient methods for synthesizing oligonucleotides. The synthesis of oligonucleotides for antisense and diagnostic applications can now be routinely accomplished. See e.g., *Methods in Molecular Biology. Vol 20: Protocols for Oligonucleotides and Analogs* pp. 165–189 (S. Agrawal, Ed., Humana Press, 1993); *Oligonucleotides and Analogues: A Practical Approach* pp. 87–108 (F. Eckstein, Ed., 1991); and Uhlmann and Peyman, supra. Agrawal and Iyer, Curr. Op. in Biotech. 6: 12 (1995); and *Antisense Research and Applications* (Crooke and Lebleu, Eds., CRC Press, Boca Raton, 1993). Early synthetic approaches included phosphodiester and phosphotriester chemistries. Khorana et al., J. Molec. Biol. 72: 209 (1972) discloses phosphodiester chemistry for oligonucleotide synthesis. Reese, Tetrahedron Lett. 34: 3143–3179 (1978), discloses phosphotriester chemistry for synthesis of oligonucleotides and polynucleotides. These early approaches have largely given way to the more efficient phosphoramidite and H-phosphonate approaches to synthesis. Beaucage and Caruthers, Tetrahedron Lett. 22: 1859–1862 (1981), discloses the use of deoxynucleoside phosphoramidites in polynucleotide synthesis. Agrawal and Zamecnik, U.S. Pat. No. 5,149,798 (1992), discloses optimized synthesis of oligonucleotides by the Hphosphonate approach.

Both of these modern approaches have been used to synthesize oligonucleotides having a variety of modified internucleotide linkages. Agrawal and Goodchild, Tetrahedron Lett. 28: 3539–3542 (1987), teaches synthesis of oligonucleotide methylphosphonates using phosphoramidite chemistry. Connolly et al., Biochemistry 23: 3443 (1984), discloses synthesis of oligonucleotide phosphorothioates using phosphoramidite chemistry. Jager et al., Biochemistry 27: 7237 (1988), discloses synthesis of oligonucleotide phosphoramidates using phosphoramidite chemistry. Agrawal et al., Proc. Natl. Acad. Sci. USA 85, 7079–7083 (1988), discloses synthesis of oligonucleotide phosphoramidates and phosphorothioates using H-phosphonate chemistry. Solid phase synthesis of oligonucleotides by any of the known approaches ordinarily involves the same generalized protocol. Briefly, this approach comprises anchoring the 3'-most nucleoside to a solid support functionalized with amino and/or hydroxyl moieties and subsequently adding the additional nucleosides in stepwise fashion. Desired internucleotide linkages are formed between the 3' functional group (e.g., phosphoramidite group) of the incoming nucleoside and the 5' hydroxyl group of the 5'-most nucleoside of the nascent, support-bound oligonucleotide.

Refinement of methodologies is still required, however, particularly when making a transition to large-scale synthesis (10 $\mu$mol to 1 mmol and higher). See Padmapriya et al., Antisense Res. Dev. 4: 185 (1994). Several modifications of the standard phosphoramidite methods have already been reported to facilitate the synthesis and isolation of oligonucleotides. See e.g., Padmapriya et al., supra; Ravikumar et al., Tetrahedron 50: 9255 (1994); Theisen et al., Nucleosides & Nucleotides 12: 43 (1994); and Iyer et al., Nucleosides & Nucleotides 14: 1349 (1995) (Kuijpers et al., Nucl. Acids Res. 18: 5197 (1990); and Reddy et al., Tetrahedron Lett. 35: 4311 (1994).

One limitation in solid phase synthesis resides in the nature of the solid phase support upon which the oligonucleotide is synthesized. A variety of solid support materials have been described for solid phase oligonucleotide synthesis, the most prevalent of which is controlled-pore glass (CPG). (See, e.g., Pon, Methods in Molec. Biol. 20: 465 (1993)). Unfortunately, CPG suffers certain limitations that prevent it from being an ideal support material. See e.g., Ron et al., Biotechniques 6: 768 (1988); McCollum et al., Nucleosides and Nucleotides 6: 821 (1987); Bardella et al., Tetrahedron Lett. 31: 6231–6234 (1990) For example, CPG is unstable under the standard ammonium hydroxide procedure that is used to deprotect the oligonucleotide and to cleave it from the solid support.

To overcome these problems, various attempts have been made to develop polymer supports to replace CPG. See e.g., Gao et al., Tetrahedron Lett. 32: 5477–5479 (1991); *The Gene Assembler™, A Fully Automated DNA Synthesizer*, Pharmacia Fine Chemicals, Uppsala, Sweden (1986). The use of organic supports in this context has been explored. Reddy et al., Tetrahedron Lett. 35: 5771–5774 (1994) discloses an organic support based on native Fractogel ("Toyopearl", TosoHaas, Philadelphia, Pa.). Fractogel, however, has inherent limitations as a support for oligonucleotide synthesis, due to its low density when packed in acetonitrile and its limited pore volume per unit bed volume. U.S. Pat. No. 5,668,268 discloses polymer supports that provide the efficiency that CPG provides without the deficiencies of CPG. However, the present inventors have discovered that certain solvents used for detritylation, notably methylene chloride, lead to channel current formation in these polymer supports.

There is, therefore, a need for processes for oligonucleotide synthesis that do not lead to channel current formation in these new supports. In addition, methylene chloride is a low boiling point chlorinated solvent, which makes its disposal problematic, and it is also expensive. Thus, there is also a need for processes for oligonucleotide synthesis that utilize cheaper solvents which are more readily disposed.

BRIEF SUMMARY OF THE INVENTION

The invention provides processes for oligonucleotide synthesis that utilize cheaper solvents which are more readily disposed than the solvents of prior art processes, and which do not lead to channel current formation in organic polymeric supports.

In a first aspect, he invention provides an improved process for solid phase oligonucleotide synthesis. In this improved process according to the invention, the improvement comprises carrying out detritylation of the nascent oligonucleotide using an arene as solvent. In certain preferred embodiments of the process according to this aspect of the invention, such synthesis is carried out using the phosphoramidite, H-phosphonate, or phosphotriester approach. This process of oligonucleotide synthesis according to the invention detritylates nascent oligonucleotides at least as efficiently as processes utilizing methylene chloride as solvent, but is less expensive, creates less toxic wastes, and does not cause channel current formation in organic polymeric solid supports.

In a second aspect, the invention provides an improved process for oligonucleotide synthesis wherein the synthesis includes coupling and detritylation steps carried out on a passivated organic polymeric support. Passivation reduces the hydrophilic character of the particle surface and increases access for the hydrophobic reagents to the nascent oligonucleotide chain, thereby improving the efficiency of the synthesis.

The processes for synthesizing oligonucleotides according to the invention are useful for synthesizing oligonucleotides on a scale ranging from small laboratory scale to large commercial scale. Thus, the processes according to the invention can be used to supply oligonucleotides for research purposes, for diagnostic purposes and for therapeutic purposes.

DETAILED DESCRIPTION OF THE PREFERRED EMBODIMENTS

Figure 1:
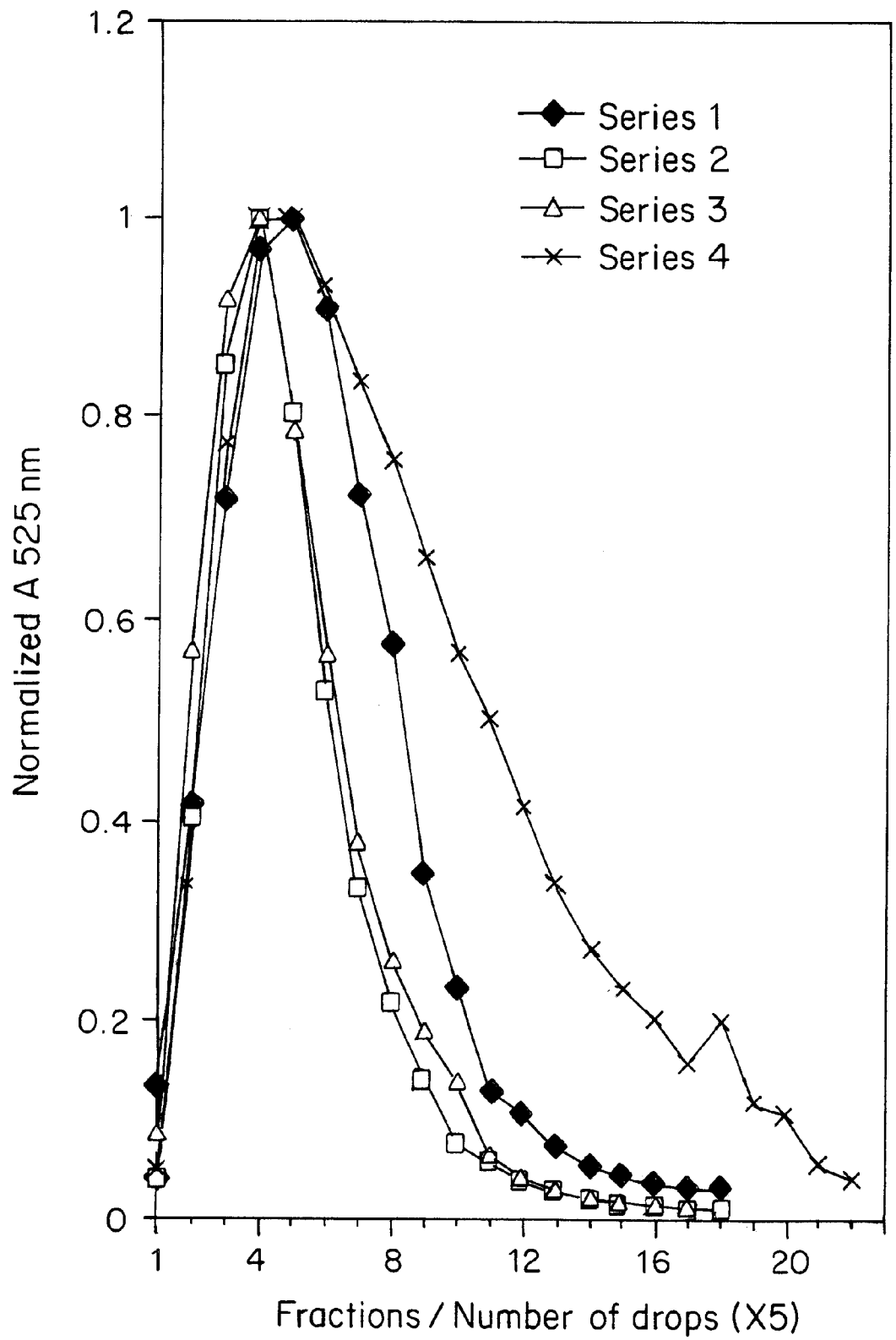
FIG. 1 shows detritylation kinetics for 3% DCA in methylene chloride (series 1), toluene (series 2), xylene (series 3) and anisole (series 4).

The invention relates to the chemical synthesis of oligonucleotides and to materials and processes that are useful in such synthesis. The patents and publications identified in this specification are within the knowledge of those skilled in this field and are hereby incorporated by reference in their entirety.

The invention provides an improved process for solid phase oligonucleotide synthesis. In this improved process according to the invention, the improvement comprises carrying out detritylation of the nascent oligonucleotide having at least one trityl group using an arene as solvent. In certain preferred embodiments of the process according to this aspect of the invention, such synthesis is carried out using the phosphoramidite, H-phosphonate, or phosphotriester approach. This process of oligonucleotide synthesis according to the invention detritylates nascent oligonucleotides at least as efficiently as processes utilizing methylene chloride as solvent, but is less expensive, creates less toxic wastes, and does not cause channel current formation in organic polymeric solid supports.

In a first aspect, the invention provides an improved process for solid phase oligonucleotide synthesis, wherein the improvement comprises detritylating a nascent oligonucleotide having one or more trityl group in an arene solvent. In certain preferred embodiments of a process according the invention, such synthesis is carried out using the phosphoramidite, H-phosphonate, or phosphotriester approach. In certain preferred embodiments, such synthesis may be solid phase synthesis or solution phase synthesis. A "nascent oligonucleotide having one or more trityl group" is intended to include any oligonucleotide in which at least one trityl moiety protects at least one hydroxy functionality.

In preferred embodiments, the arene solvent is selected from alkylbenzenes, alkenylbenzenes and alkynyl benzenes, or combinations thereof. More preferably, the alkylbenzene, alkenylbenzene and alkynylbenzene each independently have from about 1 to about 4 phenyl groups. Even more preferably, the alkylbenzene, alkenylbenzene and alkynylbenzene each independently has from about one to about 6 substituents selected from alkyl groups, alkenyl groups and alkynyl groups, or combinations thereof. Most preferably, each alkyl group, alkenyl group and alkynyl group independently has from about 1 to about 6 carbon atoms. In each embodiment the term "about" is intended to indicate a change from the exact number that creates no substantial change in the ability or effectiveness of the solvent to be used in the detritylation reaction. The most preferred embodiments, however, have the range provided by the exact numbers, as is the case for all ranges recited herein.

Alkylbenzenes are generally most preferred as solvents for detritylation. Particularly preferred are alkylbenzenes having a single phenyl ring. Examples of such particularly preferred alkylbenzenes include, without limitation, toluene, xylene, hemimellitene, pseudodocumene, mesitylene, prehnitene, isodurene, durene pentamethylbenzene, hexamethylbenzene, ethylbenzene, ethyltoluene, propylbenzene, propyltoluene, butylbenzene, pentanylbenzene, pentanyl toluene, hexanyl benzene and hexanyl toluene. Other alkylbenzenes include those having more than one phenyl ring, such as diphenylmethane, triphenylmethane, tetraphenylmethane and 1,2-diphenylethane. Preferred alkenylbenzenes include, without limitation, styrene, stilbene, diphenylethylene, triphenylethylene and tetraphenylethylene. Preferred alkynylbenzenes include, without limitation, phenylacetylene and diphenylacetylene.

In the improved process according to the invention, the detritylation step utilizes a preferred solvent in conjunction with a detritylation reagent, which effects the detritylation. Preferably, the detritylation reagent is a protic acid. As used herein, a protic acid is intended to mean a compound in which hydrogen is attached to oxygen or nitrogen and which has appreciable acidity. Particularly preferred protic acids are dichloroacetic acid (DCA) and trichloroacetic acid (TCA). The protic acid is preferably provided at a concentration (vol/vol) of from about 1% to about 5% in the solvent, most preferably about 3%. The volume of protic acid/solvent required to complete the detritylation reaction is preferably determined by observing the appearance, then the disappearance of the orange color indicative of the free trityl groups.

Oligonucleotides having any of a variety of trityl groups are amenable to the improved process according to the invention. Particularly preferred trityl groups include, without limitation, trityl, monomethoxytrityl, dimethoxytrityl, 9-phenylxanthen-9-yl and 9-p-methoxyphenylxanthen-9-yl.

In a second aspect, the invention provides an improved process for oligonucleotide synthesis wherein the synthesis includes coupling and detritylation steps carried with the nascent oligonucleotide attached to a passivated organic polymeric support. The passivated organic polymer support used in this process according to the invention comprises a plurality of passivated organic polymer microscopic particles. Preferably, the particles are generally spherical and are from about 10 microns to about 100 microns in diameter. In a particularly preferred embodiment, the particles are from about 20 to about 60 microns in diameter. Preferably, the particles are porous, to increase the surface area available for oligonucleotide attachment and synthesis. Preferably, the pore size range is from about 50 to about 4000 angstroms, as measured by mercury porosimetry. Most preferably, the pore size is from about 200 to about 1000 angstroms. An example of a particularly preferred prepassivation particle is the Toyopearl® AF AMINO-550F particle produced by TosoHaas (Philadelphia, Pa.). This particle is a copolymer of methacrylate and ethylene glycol, has a pore size of about 300 angstroms, a mean diameter of 20–60 microns, a density of 0.36 g/ml after swelling in acetonitrile and a pore volume of 0.54 ml/1 ml of bed volume.

The material for the base particle is preferably a polymer or copolymer comprising acrylate, methacrylate or polystyrene. Preferred copolymers include, but are not limited to, methacrylate/ethylene glycol (Toyopearl, TosoHaas, Philadelphia, Pa.), dimethacrylate/pentaerythritol, polystyrene/divinylbenzene, copolymers of pentaerythritol dimethacrylate and a methacrylate monomer, copolymers of a hydrophilic monomer selected from the group consisting of hydroxyalkyl methacrylates, aminoalkyl methacrylates, N-vinylpyrrolidone, acrylonitrile, methacrylonitrile, acrylic acid, methacrylic acid, and mixtures thereof, with a substantially hydrophobic monomer selected from the group consisting of ethylene dimethacrylate, ethylene diacrylate, methylenebisacrylamide, diethylene glycol methacrylamide, poly (ethyleneglycol) methacrylamide, neopentyl glycol diacrylate, neopentyl glycol dimethacrylate, trimethylol propane trimethacrylate, divinylbenzene, and mixtures thereof, copolymers of polar monomers such as hydroxyalkyl acrylates and hydroxyalkyl methacrylates, with non-polar monomers such as alkyl acrylates and methacrylates, together with cross-linking agents such as alkylene diacrylates and methacrylates, and homopolymers of pentaerythritol dimethacrylate. These and other appropriate organic polymers are known in the art and can be synthesized by art recognized techniques, such as those taught in U.S. Pat. Nos. 4,224,415, 4,256,840, 4,297,220, 4,501,816, 4,246,362, 4,184,020, 4,135,892 and 3,925,267, each of which is hereby incorporated by reference. Each particle has amino groups and/or hydroxyl groups covalently bound to the particle surface, including surface areas within the pores. For purposes of the invention, any area which is at, attached to, or within the particle boundary and in fluid communication with an extraparticle area is considered to be a part of the particle surface. Amino and/or hydroxyl functionalization of organic polymer particles is well known in the art, and is described, for example in U.S. Pat. Nos. 4,245,005 and 5,030,352, each of which is hereby incorporated by reference. In addition, such amino and/or hydroxyl functionalized particles are commercially available from several sources, including TosoHaas (Philadelphia, Pa.) and Merck (Darmstadt, Germany).

Each particle further has nucleosides covalently bound to some of the amino and/or hydroxyl groups. Loading of the nucleosides onto the particles can be carried out as described herein, or by any of the procedures that are well known in the art (see e.g., Reddy et al., Tetrahedron Lett. 35: 5771–5774 (1994); Bhongle et al., Synthetic Communications 25: 3671–3679 (1995)). However, at high nucleoside loading densities, it is not possible to have every amino and/or hydroxyl group bound to a nucleoside. Consequently, some of the amino and/ or hydroxyl groups will remain free, which imparts a hydrophilic character to the particle surface.

A unique feature of organic polymer particles used in the process according to the invention is that they are passivated, i.e., at least some of the amino and/or hydroxyl groups that are not covalently bound to nucleosides are covalently bound to hydrophobic passivating groups, such as aroyl groups. Preferred aroyl groups for polymer supports according to this aspect of the invention include those having the structure I:

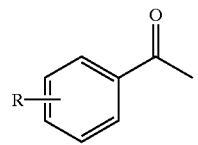

wherein there are from 0 to 3 R groups and each R group is independently a lower alkyl group, a phenyl group, a halogen, or a nitro goup. Passivation with such a structure reduces the hydrophilic character of the particle surface and increases access for the hydrophobic reagents to the nascent oligonucleotide chain, thereby improving the efficiency of the synthesis. Preferably, of the amino and/or hydroxyl groups that are not covalently bound to nucleosides, from about 50 per cent to about all of such groups are covalently bound to a hydrophobic passivating group, and most preferably from about 90% to about all.

Organic polymer supports are passivated by contacting an organic polymer support particle having a surface that has both covalently bound nucleosides and covalently bound free amino and/or hydroxyl groups with an appropriate passivating reagent. An appropriate passivating reagent is a reagent that is capable of causing a hydrophobic passivating group, such as an aroyl group, to become covalently linked to free amino and/or hydroxyl groups on the surface of the particle. Preferred passivating reagents include acid anhydrides of aroyl groups or aroyl chlorides. Most preferably, the passivating reagent is a mixture comprising benzoic anhydride and dimethylaminopyridine.

The processes according to the invention are useful for synthesizing oligonucleotides on a scale ranging from small laboratory scale to large commercial scale. Thus, the processes according to the invention can be used to supply oligonucleotides for research purposes, for diagnostic purposes and for therapeutic purposes.

The following examples are intended to further illustrate certain preferred embodiments of the invention and are not intended to be limiting in nature.

EXAMPLE 1

Trityl-Nucleoside Derivatization and Passivation of Organic Polymer Solid Supports A mixture of hydroxybenzotriazole (0.1 g), 1,3-diisopropylcarbodiimide (1 ml) and 5% pyridine/acetonitrile (100 ml) was hand shaken until a clear solution was obtained. To the solution was added 20 g dried AF AMINO550F organic polymer beads derivatized with amino groups to an amino group density of 244–400 micromoles/g (Toyopearl, TosoHaas, Philadelphia, Pa.). Next, 1.5 g DMT-thymidine succinic acid was added and the mixture was shaken in an orbital shaker at 170 rpm for about six hours at room temperature. The mixture was then filtered with a Buchner funnel and the beads were washed five times with 100 ml 5% pyridine/acetonitrile. A solution of 15 g benzoic anhydride and 3 g dimethylaminopyridine in 100 ml 20% pyridine/acetonitrile was added and the mixture was shaken in an orbital shaker at 170 rpm overnight at room temperature. The mixture was then filtered in a Buchner funnel and washed five times with 100 ml 5% pyridine/acetonitrile. Next, the beads were treated with a solution of 10% acetic anhydride, 10% N-methylimidazole, 20% pyridine in tetrahydrofuran overnight at room temperature. The mixture was filtered in a Buchner funnel and washed five times in 100 ml acetonitrile+100 ml methylene chloride, then the beads were vaccuum dried overnight. The level of nucleoside loading was determined using a conventional DMT cation assay (Gait, *Oligonucleotide Synthesis. A Practical Approach.* p. 107, IRL Press (1984). After swelling in acetonitrile, the passivated beads were found to be approximately 10% denser than the beads prepared according to Example 2 below.

EXAMPLE 2

Assessment of Detritylation Kinetics

Dimethoxytrityl thymidine loaded polymer beads were prepared according to Example 1 and 1 gram was placed in a 10 ml syringe equipped with a filter at the base. Solvent containing 3% DCA was allowed to drip through the syringe by gravity. The results are shown in Table 1. The detritylation rate using toluene as solvent was comparable to that using methylene chloride. The rate in acetonitrile was far slower.

TABLE 1

| solvents | polarity index | density | vol 1 g swelled beads | detritylating vol 3% DCA |
| --- | --- | --- | --- | --- |
| methylene chloride | 3.4 | 1.325 | 5.0 | 5 ml |
| toluene | 2.3 | 0.865 | 4.6 | 5 ml |
| acetonitrile | 6.2 | 0.786 | 4.5 | no detritylation |
| 9:1 methylene chloride/acetonitrile | | | 5.0 | 5 ml |
| 7:3 methylene chloride/acetonitrile | | | 4.8 | 20 ml |
| 3:7 methylene chloride/acetonitrile | | | 4.7 | no detritylation |
| 8:2 methylene chloride/toluene | | | 5.0 | |
| 7:3 methylene chloride/toluene | | | 4.8 | 5 ml |
| 5:5 methylene chloride/toluene | | | 4.9 | 5 ml |

EXAMPLE 3

Further Assessment of Detritylation Kinetics

Thirty mg to 30.5 mg dimethoxytrityl thymidine-loaded CPG (loaded at 71.4 $\mu$mol/g) was placed in a filter-equipped syringe. Before detritylation, CPG was rinsed once with acetonitrile by drawing up and expelling acetonitrile. Three % DCA in solvent was dropped into the syringe through a separate funnel. Five drops from the needle of the syringe per fraction were collected into a 4 ml test tube until no more orange color eluted from the syringe. All fractions were diluted to 3.5 ml (+/−0.1 ml) with 3% TCA in methylene chloride and the concentration of free DMT was measured by absorbance at 525 nm. Table 2 shows $A_{525}$ values for 6 DCA/solvent systems.

TABLE 2

| | $CH_2Cl_2$ | toluene | xylene | anisole | hexane | $(Bz)_2O$ |
| --- | --- | --- | --- | --- | --- | --- |
| frac 1 | 0.208 | 0.085 | 0.175 | 0.048 | | |
| frac 2 | 0.660 | 0.870 | 1.120 | 0.369 | | |

TABLE 2-continued

| | $CH_2Cl_2$ | toluene | xylene | anisole | hexane | $(Bz)_2O$ |
| --- | --- | --- | --- | --- | --- | --- |
| frac 3 | 1.125 | 1.847 | 1.801 | 0.806 | | |
| fract 4 | 1.518 | 2.165 | 1.959 | 1.039 | | |
| frac 5 | 1.567 | 1.740 | 1.549 | 1.044 | | |
| fract 6 | 1.419 | 1.148 | 1.110 | 0.964 | | |
| frac 7 | 1.131 | 0.723 | 0.747 | 0.872 | | |
| frac 8 | 0.902 | 0.475 | 0.511 | 0.780 | | |
| frac 9 | 0.541 | 0.315 | 0.377 | 0.688 | | |
| frac 10 | 0.362 | 0.168 | 0.227 | 0.590 | | |
| frac 11 | 0.206 | 0.121 | 0.128 | 0.523 | | |
| frac 12 | 0.170 | 0.088 | 0.089 | 0.434 | | |
| frac 13 | 0.113 | 0.061 | 0.063 | 0.345 | | |
| frac 14 | 0.083 | 0.042 | 0.046 | 0.282 | | |
| frac 15 | 0.064 | 0.032 | 0.033 | 0.240 | | |
| frac 16 | 0.050 | 0.026 | 0.026 | 0.210 | | |
| frac 17 | 0.048 | 0.021 | 0.021 | 0.162 | | |
| frac 18 | 0.052 | 0.017 | | 0.208 | | |
| frac 19 | | | | 0.120 | | |
| frac 20 | | | | 0.108 | | |
| frac 21 | | | | 0.055 | | |
| | | | | 0.038 | | |
| total | 10.219 | 9.994 | 9.982 | 9.925 | 0 | 0 |

Normalized $A_{525}$ values versus fractions (5 drop/fraction) are shown in FIG. 1. Both toluene and xylene give sharper peaks than methylene chloride, indicating that they are both better detritylation and elution solvents than methylene chloride. Anisole requires a greater volume of 3% DCA solution to complete detritylation, probably because of its ether structure, which will compete for protonation. Hexane supports detritylation (orange color was observed) but cannot elute the free trityl from the CPG. No detritylation was observed for benzyl ether, probably due to DCA reacting with benzyl ether to liberate a stable benzyl cation.

EXAMPLE 4

Synthesis of Oligonucleotides

To test the effectiveness of various detritylation solvents for oligonucleotide synthesis, the following synthesis were performed. In each synthesis, the same oligonucleotide phosphorothioate was prepared. A 25-mer phosphorothioate oligonucleotide was synthesized at 1 $\mu$mol scale and a 20-mer phosphorothioate was synthesized at 400 $\mu$mol scale. Syntheses were conducted on CPG at 1 $\mu$mol scale on an Expedite synthesizer (Perseptive Biosystems, Framingham, Mass.) and at 400 $\mu$mol scale on a Pharmacia Oligopilot II synthesizer (Uppsala, Sweden). In all syntheses, standard cyanoethyl phosphoramidites were used in 1.5 fold excess. Detritylation used 3% TCA in methylene chloride or toluene for the 25-mer and 3% DCA in methylene chloride or toluene for the 20-mer. Crude 25-mers were analyzed by capillary electrophoresis. Crude 20-mers were analyzed by ion-exchange HPLC. Area percent results are shown in Table 3. Toluene was comparable to methylene chloride as a solvent for detritylation in these experiments.

TABLE 3

| | 3% DCA in $CH_2Cl_2$ | 3% DCA in toluene | 3% TCA in $CH_2Cl_2$ | 3% TCA in toluene |
| --- | --- | --- | --- | --- |
| 25-mer | | | 86.8% | 83.1% |
| 20-mer | 69% | 67% | | |

Those skilled in the art will recognize that many equivalents to the products and processes according to the invention can be made by making insubstantial changes to such products and processes. The following claims are intended to encompass such equivalents.

What is claimed is:

1. An improved process for solid phase oligonucleotide synthesis, the improvement comprising detritylating the nascent oligonucleotide having one or more trityl group in an arene solvent.

2. The improved process according to claim 1, wherein the arene solvent is selected from alkylbenzenes, alkenylbenzenes and alkynyl benzenes, or combinations thereof.

3. The improved process according to claim 2, wherein the alkylbenzene, alkenylbenzene and alkynylbenzene each independently have from about 1 to about 4 phenyl groups.

4. The improved process according to claim 3, wherein the alkylbenzene, alkenylbenzene and alkynylbenzene each independently has from about one to about 3 substituents selected from alkyl groups, alkenyl groups and alkynyl groups, or combinations thereof.

5. The improved process according to claim 4, wherein each alkyl group, alkenyl group and alkynyl group independently has from about 1 to about 6 carbon atoms.

6. The improved process according to claim 5, wherein each alkyl group is a methyl group.

7. The improved process according to claim 6, wherein the solvent is toluene, xylene, or combinations thereof.

8. The improved process according to claim 1, wherein the detritylation is effected by a protic acid.

9. The improved process according to claim 8, wherein the protic acid is DCA or TCA.

10. The improved process according to claim 9, wherein at least one trityl group is selected from trityl, monomethoxytrityl, dimethoxytrityl, 9-phenylxanthen-9-yl and 9-p-methoxyphenylxanthen-9-yl.

11. The improved process according to claim 1, wherein the oligonucleotide is attached to a passivated organic polymer support.

* * * * *

UNITED STATES PATENT AND TRADEMARK OFFICE
CERTIFICATE OF CORRECTION

PATENT NO. : 6,538,128 B1
DATED : March 25, 2003
INVENTOR(S) : Guangrong Zhang and Jin-Yan Tang It is certified that error appears in the above-identified patent and that said Letters Patent is hereby corrected as shown below:

<u>Title page,</u>
Item [22], please delete "Mar. 22, 1999" and insert therefor -- Sept. 4, 1998 --

Signed and Sealed this

Fifteenth Day of July, 2003

JAMES E. ROGAN
*Director of the United States Patent and Trademark Office*